June 19, 1956 L. L. BROOKS Plant Pat. 1,483

AZALEA PLANT

Filed May 6, 1955

Inventor
LENARD L. BROOKS

BY Clarence A. O'Brien
and Harvey B. Jacobson
Attorneys

United States Patent Office

Plant Pat. 1,483

Patented June 19, 1956

1,483
AZALEA PLANT

Lenard L. Brooks, Modesto, Calif.

Application May 6, 1955, Serial No. 506,685
1 Claim. (Cl. 47—50)

This invention is directed to a new and distinct variety of azalea plant, such plant being characterized particularly by its large perfectly formed, hose in hose flowers, with an undertone of orange, its ease of reproduction on its own roots, its large, glossy deep green leaves, its high value as a greenhouse forcing or garden variety, and its much branched compact habit of growth.

The instant variety is a cross produced in the experimental garden of my nursery at Modesto, California; the cross being made by pollen from the Kurume azalea Hexe on the Belgian Indica azalea Wm. Van Orange, neither of the parent varieties being patented.

The cross as produced was recognized by me as possessing novel characteristics and appeared suitable for commercial use. It was therefore taken for propagation by cuttings, and the first cuttings produced azalea plants which carried forward all the distinguishing features of the parent.

The original asexual reproduction of the variety by cuttings was carried out in my experimental garden at Modesto, California. Subsequent propagations of the variety by cuttings further evidences that the variety is fixed in its floricultural characteristics.

Referring now more specifically to the botanical details of the new and distinct variety of azalea plant, the following is an outline description of the same:

PLANT

Form: Many branched, rounded, symmetrical form. In the young plants the height and breadth are about equal, but as they attain age the breadth gradually becomes greater than the height.

Growing habit: Dense and bushy with heavy dark green foliage. The rate of growth is more rapid than most of the Indica azaleas. The rate of growth will compare favorably with most of the Kurume azaleas.

Blooming habit: It blooms out evenly over the entire plant when forced in the greenhouse or flowered naturally in the garden. Usually two flowers (and often more) are produced on each stem.

Blooming season: March-April in central California. It is an excellent mid-season forcer for the greenhouse.

Foliage:

*Size.*—Mature foliage 1½″ to 2½″ long and ⅞″ to 1¼″ wide.

*Color.*—Tyrolian green.

*Shape.*—Broadly ovate, not pointed.

*Aspect.*—Glossy with some hairs on both sides.

*Texture.*—Medium.

*Edges.*—Very slight serrations and hairs.

*Ribs and veins.*—Normal.

Flower:

*Size.*—Average 2½″ to 3″.

*Borne.*—Usually two to each stem and frequently more.

*Stem.*—Medium length, with sufficient strength to hold the flowers properly.

*Form.*—Hose in hose, with a strong tendency to doubleness inherited from the Indica. The petals are pleasingly ruffled.

*Permanence.*—Long lasting without fading or changing color as the flowers age.

Figure 1:
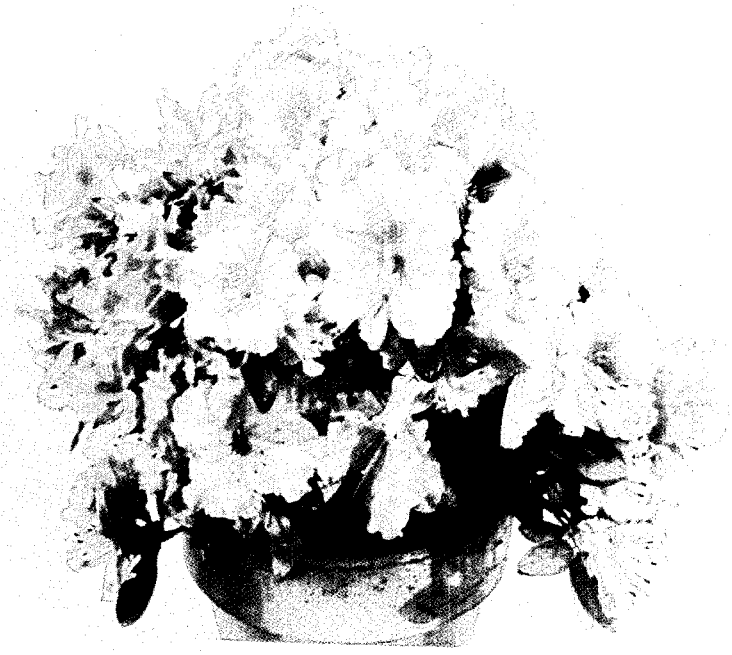
Fig. 1 is a perspective view showing the flowers in bloom.
Figure 2:
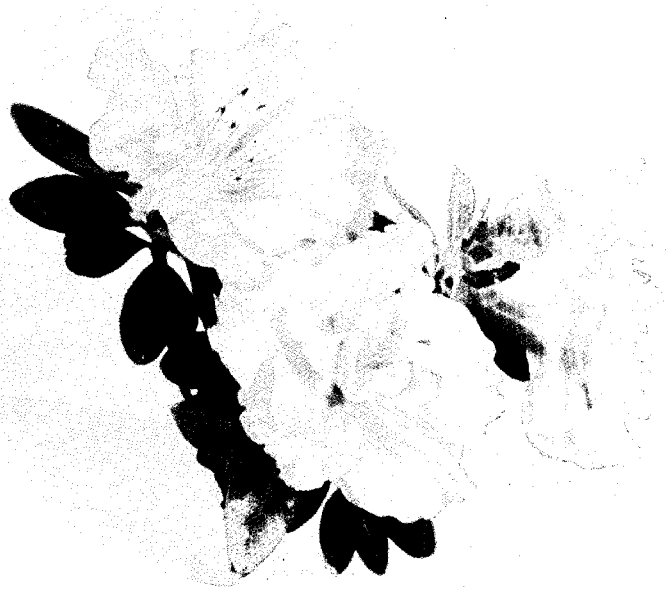
Fig. 2 is a perspective view of a stem, with leaves and flowers.

*Petalage.*—Five petals on each hose or flower, often having antherferus petaloids in the center, which are in addition to the regular hose in hose flower. (See lower flower in Fig. 2.)

*Color.*—Base of petals has a distinct orange tone, giving the flower a bright, lively appearance.

Petals:

*Texture.*—Heavy.

*Appearance.*—Velvety, with edges pleasingly ruffled.

*Size.*—1″ to 1⅛″ wide and 1½″ to 1¾″ long.

*Shape.*—Broadly ovate, not pointed, narrowing abruptly at lower end.

*Arrangement.*—Normal Kurume type—one flower within the other.

*Persistence.*—Remains firm without wilting or noticeable change in color until the flower is ready to fall.

Reproductive organs:

*Stamens.*—Five, often developing petaloids in this variety. Anther is blackish and filament is about the same color as the outer edges of petals.

*Pollen.*—White.

*Style.*—About the same color as petals with the stigma darker. Style and stigma usually deformed when the stamens develop petaloids.

*Ovaries.*—Usually normal, but not always.

The color designations according to "A Dictionary of Color" by Maerz and Paul are as follows:

| Part | Color | Plate | Letter | Number |
|---|---|---|---|---|
| Foliage: | | | | |
| New leaves | | 23 | L | 2 to 5 |
| Mature leaves | | 32 | A | 12 |
| Stems (new growth) | | 16 | E | 9 |
| Flower: | | | | |
| Outer edge of petals | | 3 | H | 6 |
| Base of petals | | 4 | L | 11 |

Inasmuch as this variety is from the same cross as my variety "Redwing" (Plant Patent No. 1159), there are some similarities, but there are the following principal differences:

1. The foliage is broader, but not pointed, and the plant has a brighter, smoother appearance.

2. The plant does not grow quite as fast, but it branches easier and requires less shearing to produce a well branched plant.

3. The flower itself is an important point of difference. Basically, the color is same, except this variety has more blue. More importantly, this variety always opens with both hoses perfect, as contrasted with the "redwing," which very often opens with an imperfect outer hose. This gives the flower a ragged look, and quite often an entire crop will bloom with the imperfect hose, materially lowering the sales value.

Tests indicate that this variety has hardiness equal to Redwing and starts just as easily from cuttings.

Having thus described the invention, I claim:

A new and distinct variety of azalea plant substantially as shown and described, of the Kurume class, comprised of a cross between the Kurume azalea Hexe and the Belgian Indica azalea Wm. Van Orange, characterized particularly by its large and invariably perfectly formed hose in hose flowers bearing an undertone of orange; by its ease of reproduction on its own roots; by its high value as a greenhouse forcing or garden variety; by its much branched, compact habit of growth, and its large, glossy deep green leaves.

No references cited.